(12) United States Patent
Gardella, Jr. et al.

(10) Patent No.: US 6,864,090 B2
(45) Date of Patent: Mar. 8, 2005

(54) METHOD FOR TESTING THE DEGRADATION OF POLYMERIC MATERIALS

(75) Inventors: Joseph A. Gardella, Jr., Buffalo, NY (US); Jiaxing Chen, Angleton, TX (US); Norma L. Hernandez de Gatica, Lakewood, OH (US); Joo-Woon Lee, Austin, TX (US)

(73) Assignee: Research Foundation of State University of New York at Buffalo, Amherst, NY (US)

( * ) Notice: Subject to any disclaimer, the term of this patent is extended or adjusted under 35 U.S.C. 154(b) by 0 days.

(21) Appl. No.: 10/690,196

(22) Filed: Oct. 21, 2003

(65) Prior Publication Data

US 2004/0203161 A1 Oct. 14, 2004

Related U.S. Application Data

(63) Continuation of application No. 10/331,802, filed on Apr. 7, 2003, now Pat. No. 6,670,190, which is a continuation-in-part of application No. 09/680,701, filed on Oct. 6, 2000, now abandoned.
(60) Provisional application No. 60/157,964, filed on Oct. 6, 1999.

(51) Int. Cl.[7] .......................... G01N 33/00; G01N 24/00
(52) U.S. Cl. .......................... 436/34; 326/173; 326/174; 326/85
(58) Field of Search ............................ 436/173, 34, 85, 436/174

(56) References Cited

PUBLICATIONS

Saito et al. "TOF–SIMS analysis of chemical state changes in cresol–novolak photresist surface caused by O2 plasma downstream", Applied Surface Science (1999), 142(1–4), 460–464.*

Davies et all. "Probing the surface chemical structure of some novel poly(ortho esters) prepared with N–methyl and N–phenyl ethanolamine by . . . (ToF–SIMS)", Polymers for Advanced Technologies, Sep. 1999, v. 3, pp. 293–301.*

Chen et al. "Time–of–Flight Secondary Ion Mass Spectrometry studies of in vitro hydrolytic degradation of biodegradable polymers", Macromolecules, 1999, v. 32, pp. 7380–7388.*

Chen et al. "Time–of–Flight Secondary Ion Mass spectrometry studies of hydrolytic degradation kinetics at the surfaced of poly(glycolic acid)", Macromolecules, 2000, v. 33, pp. 4726–4732.*

Davies et al. "Probing the surface chemical structure of some novel poly(ortho esters) prepared with N–methyl– and N–phenylethanolamine by time–of–flight secondary ion mass spectrometry (ToF–SIMS)", Polymers for Advanced Technologies (1992), 3(6), 293–301.*

Short et al."TOF SIMS in polymer surface studies", Vacuum (1993), 44(11–12), 1143–60.*

Lhoest et al. : "PMMA surface modification under keV and MeV ion bombardment in relation to mammalian cell adhesion", Nuclear Instruments & Methods in Physics Research, Section B: (1995), 105(1–4), 322–7.*

Weidner et al. "Plasmaoxidative and chemical degradation of poly(ethylene terephthalate) studied by matrix–assisted laser desorption/ionization mass spectrometry", Rapid Communications in Mass Spectrometry (1996), 10(1), 40–6.*

* cited by examiner

*Primary Examiner*—Yelena G. Gakh
(74) *Attorney, Agent, or Firm*—Hodgson Russ LLP

(57) ABSTRACT

The present invention provides a novel method for monitoring the reaction kinetics of the biodegradable polymers, and the surface concentration of a drug in a polymer blend matrix. Detailed information on surface concentration, degradation rates, degradation kinetics and mechanism, is provided by using Time-of-Flight Secondary Ion Mass Spectrometry (ToF SIMS) measurements. Also provided is a method for determining oligomers in hydrolyzed biodegradable polymers.

13 Claims, 14 Drawing Sheets

METHOD FOR TESTING THE DEGRADATION OF POLYMERIC MATERIALS

This application is a continuation of U.S. patent application Ser. No. 10/331,802 filed Apr. 7, 2003, now U.S. Pat. No. 6,670,190, which is a continuation-in-part of U.S. patent application Ser. No. 09/680,701 filed Oct. 6, 2000, now abandoned, which in turn claims priority to U.S. Provisional Patent Application No. 60/157,964, filed on Oct. 6, 1999.

This invention was made with government support under grants CHE9704996 and CHE0079114 from the National Science Foundation. The government has certain rights in the invention.

BACKGROUND OF THE INVENTION

The present invention relates generally to the field of degradable polymers. More particularly, the present invention provides a method for determining oligomeric degradation products of biodegradable polymers either alone or simultaneously with surface concentration of drug in polymer-drug blend matrices and the drug release characteristics of such blends. This information is useful in determining degradation reaction kinetics of biodegradable polymers and biodegradable polymer-drug blend matrices and the drug release characteristics of such blends. Synthetic biodegradable polymers have been used in clinical applications for decades. Some relevant applications include surgical implants, wound healing materials, absorbable sutures and drug delivery devices. Among issues important in developing biomedical applications based on polymer biodegradability are the properties of degradation (such as rate, mechanism, by products, etc.) of the polymer material. The study of hydrolytic degradation of biodegradable polymers has been a research focus in the past few decades with in vivo investigations of biopolymer implants being the major clinical investigation method. Direct monitoring of the weight loss of polymer implants and histological observations provides macroscopic information on the hydrolytic degradation. A drawback of this method is that it is very time consuming.

For the in vitro investigation of hydrolytic degradation of biodegradable polymers, many bulk characterizations have been developed. Properties such as tensile strength, thermal properties, mass loss, and decrease in molecular weight have been measured. Techniques used include: differential scanning calorimetry (DSC), gravimetry, gel permeation chromatography (GPC), size exclusion chromatography (SEC), FTIR, NMR, X-ray diffraction and laser diffractometry.

Among the surface sensitive microscopic and spectroscopic techniques, methods such as scanning electron spectroscopy (SEM) and atomic/scanning force microscopy have become important means for studying biodegradation of polymers. The surface microscopic techniques, however, do not provide chemical compositional or structural information.

A class of biodegradable polymer that has attracted considerable attention for the design of novel drug delivery systems is the polyesters. These include poly-(α-hydroxy acids), poly(β-hydroxy acids), poly(α-malic acids), pseudopoly(α-amino acids), their copolymers, and mixtures thereof. Of particular interest are the polyesters with pendant carboxylic acid groups. These carboxylic acid groups may be functionalized to manipulate material properties and are thought to have a catalytic effect on the hydrolytic scission of the ester bonds, increasing the degradation rate.

The drug release kinetics from drug/biodegradable polymer blend matrices is complicated due to both polymer erosion and drug diffusion through preformed microporous channels within the matrices. Factors such as morphology and crystallinity of a polymer, formulation, drug molecular size and solubility may have significant influence not only on the degradation of drug delivery devices, but also on the release profile of a drug. Furthermore, it has been reported that it is difficult to predictably control drug release over a desired period. This is suspected as being due more to an initial burst (rapid release) of drug combined with the process of relatively faster drug diffusion than polymer degradation of the matrices. Although a number of studies have been directed toward drug release profiles and correlating these results with polymer degradation kinetics, little attempt has been made to simultaneously determine both, especially with respect to the surface/interface chemistry for the induction phase of bulk erosion of drug/biodegradable polymer blend matrices.

Thus, conventional techniques do not provide information to quantitatively describe the initial burst of drug release with the polymer degradation kinetics at the induction phase of bulk erosion of the blend matrices. Thus, there is a pressing need to develop powerful and fast methods for evaluating and screening the degradation kinetics of biodegradable polymers and drug release profile in the induction period of bulk erosion of biodegradable polymer blend matrices.

SUMMARY OF THE INVENTION

The present invention provides a novel method for simultaneously determining both surface concentration of a drug and degradation kinetics of a biodegradable polymer/drug blend matrix by using Time-of-Flight Secondary Ion Mass Spectrometry (ToF SIMS) measurements. The method comprises simultaneously determining surface concentration of a drug in the polymer/drug matrix and reaction kinetics of a degradable polymer in the polymer/drug matrix by the following steps: providing a polymer/drug matrix, initiating degradation of the polymer/drug matrix, subjecting the degraded polymer/drug matrix to high mass and low mass ToF SIMS spectral analysis, identifying and quantifying oligomers from the high mass ToF SIMS over a period of time, identifying and quantifying surface drug from the low mass ToF SIMS spectra over the same period of time, and calculating the rate of formation of one or more oligomers and the rate of change of surface concentration of drug.

In yet a further embodiment of the present invention, oligomers of a hydrolyzed biodegradable polymer are identified and quantified by the following steps: providing a biodegradable polymer, initiating hydrolytic degradation of the biodegradable polymer, subjecting the degraded biodegradable polymer to high mass ToF SIMS spectral analysis and identifying and quantifying oligomers from the high mass ToF SIMS spectral analysis.

DETAILED DESCRIPTION OF THE INVENTION

Figure 1:
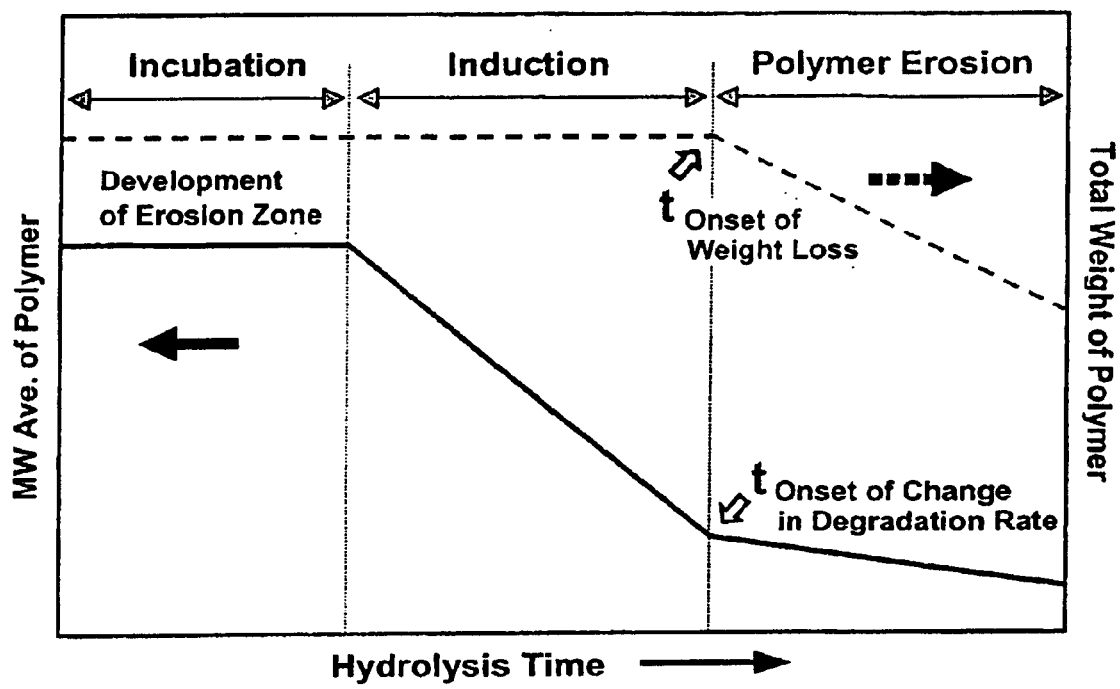
FIG. 1 is a representation of the three major steps in the course of polymer erosion.

The expression "polymer blend matrix" and words of similar effect as utilized herein refer to a mixture of at least one polymeric component and at least one non-polymeric component. Typical blend matrices will contain between about 1 to about 99 and about 99 to about 1 wt % polymer to non-polymer.

The term "drug" as utilized herein to describe suitable blend matrices refers to chemical compositions and is intended to be interpreted in its broadest sense. Therefore "drug" would include substances used in the diagnosis, treatment or prevention of disease or as a component of medication as well as other chemicals or dyes.

The term "degradation" as utilized herein refers to the disruption of the chemical linkages that form a polymeric blend matrix from a number of one or more different monomeric subunits. Therefore degradation may be a result of chemical activities such as solvation, desorbtion, dissociation, hydrolysis, dissolution, oxidation, reduction, photolysis, etc. as well as physical activities that may erode a polymeric blend matrix such as diffusion, abrasion, cracking, peeling, mechanical breakage, spinodal decomposition, etc. or any combination of these chemical and physical activities.

The present invention provides a novel method for simultaneously and independently determining both surface concentration of a drug and degradation kinetics of degradable polymer/drug blend matrix by using Time-of-Flight Secondary Ion Mass Spectrometry (ToF SIMS) measurements. The method can be used for in vitro studies of polymeric biomaterials such as those intended for use as drug delivery systems and significantly reduce the need of in vivo studies. However, when desirable, the method can also be used for studies of in vivo polymer degradation.

The invention provides a method for simultaneously determining surface concentration of a drug in the blend matrix and reaction kinetics of a degradable polymer in a blend matrix comprising the following steps: providing a polymer/drug matrix, initiating degradation of the polymer/drug matrix, subjecting the degraded polymer/drug matrix to high mass and low mass ToF SIMS spectral analysis, identifying and quantifying oligomers from the high mass ToF SIMS over a period of time, identifying and quantifying surface drug from the ToF SIMS spectra over the same period of time, and calculating the rate of formation of one or more oligomers and the rate of change of surface concentration of drug.

In yet a further embodiment of the present invention, oligomers of a hydrolyzed biodegradable polymer are identified and quantified by the following steps: providing a biodegradable polymer, initiating hydrolytic degradation of the biodegradable polymer, subjecting the degraded biodegradable polymer to high mass ToF SIMS spectral analysis and identifying and quantifying oligomers from the high mass ToF SIMS spectral analysis.

In certain embodiments of the invention herein the analysis is begun by obtaining specimens and mounting them on suitable sample holders. An example of a suitable specimen is a thin film specimen. Methods of preparing thin film specimens of the blend matrix include, for example, melt pressing, melt casting, spin coating, solvent casting, monolayer film production, lamination, etc.

Non-limiting examples of polymers useful in the practice of the invention herein include polyesters, polyanhydrides, copolymers of polyesters and polyanhydrides and mixtures thereof. When the polymer component is a polyester, the polyester may be formed of poly($\alpha$-hydroxy acids), poly($\beta$-hydroxy acids), poly($\alpha$-malic acids), pseudo poly($\alpha$-amino acids), copolymers thereof and mixtures thereof. When the polymer component is a polyanhydride, the polyanhydride may be formed of homo-polyanhydrides of sebacic acid, homo-polyanhydrides of fumaric acid, random co-polyanhydrides of sebacic and fumaric acids, and mixtures thereof.

When the specimen is a blend matrix, the non-polymeric component can be any of one or more broad types of materials. Non-limiting examples of these non-polymeric materials would include: catalysts, chemicals, dyes, low molecular weight drugs, hydrophilic drugs, hydrophobic drugs, peptides, short chain length polypeptides and mixtures thereof.

As a reference TOF-SIMS spectrum for the untreated specimens, the surface of the specimens is doped with, for example, $Na^+$ using 1 N NaCl solution, followed by suitable drying, for example, quick dry in vacuum at least for 24 hours. Other doping ions such as potassium and silver may be suitable depending upon the specific application. The choice of dopant is within the purview of one skilled in the art.

Degradation of the specimen can be performed by exposing the material to lytic solution acids, bases, etc., abrading the specimen, solvent immersion, buffer solution immersion. Therefore, methods of degrading would include solvating, desorbing, dissociating, hydrolyzing, dissolving, diffusing, abrading and combinations thereof. The degradation can take place at any suitable temperature, for example, room temperature, body temperature, etc. When degradation is accomplished by hydrolyzing in buffer solution, the buffer solution can be various saline buffers having a pH between about 2.0 and about 12.0 and containing ions such as phosphate, acetate, carbonate, biphthalate, or mixtures thereof.

The specimen can be dried before and/or after degradation by processes including but not limited to: contacting the specimen with a graded series of dehydrating liquids; subjecting the specimen to microwave energy; subjecting the specimen to heat at ambient or sub-atmospheric pressures, e.g., drying oven at temperatures from about 35° C. to about 85° C., or vacuum oven at temperatures from about 35° C. to about 85° C.; subjecting the specimen to sub-atmospheric pressure in the presence or absence of a desiccant, e.g., closed container subjected to vacuum optionally containing a desiccant such as anhydrous calcium chloride, anhydrous silica gel or the like; etc.

TOF-SIMS analysis can be performed with any appropriate instrument. A description of ToF-SIMS instruments can be found in "ToF-Sims, Surface Analysis by Mass Spectrometry", Eds. J. C. Vickerman and David Briggs; I.M. Publications, U.K. (2001).

Figure 2:
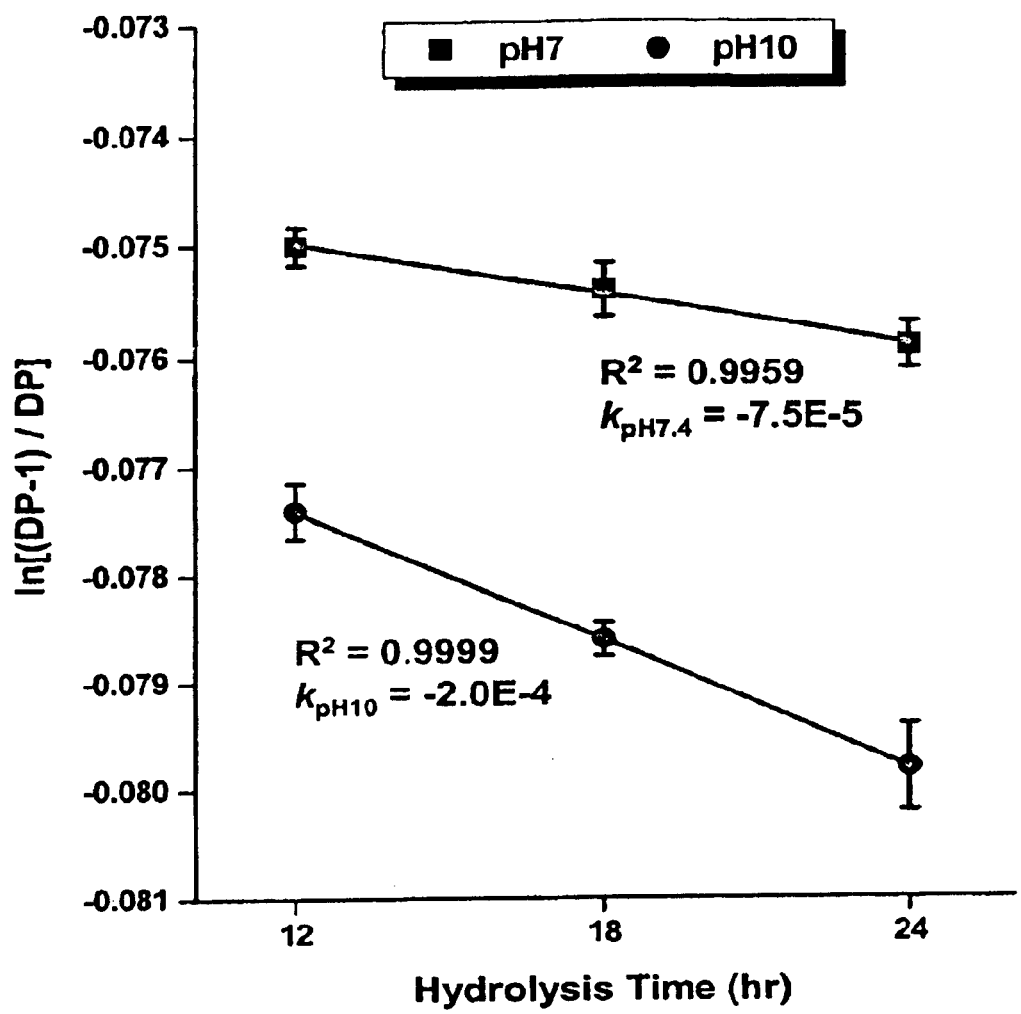
FIG. 2 is a plot showing degradation kinetics at varying pH.

To extract a MW average from the distribution of oligomeric degradation products, the spectra are analyzed using a conventional statistical averaging definition for the number average molecular weight ($M_n$) This is then converted to degree of polymerization (DP). For example, in the case of PLLA, the average DP at time t is defined as the repeating number of $M_n$ of PLLA degradation products:

$$DP=(M_n-18)/(72) \qquad (1)$$

where 18 is the mass of both end-groups and 72 is the mass of PLLA repeat unit. The kinetics expression for the surface degradation by hydrolytic chain scissions of PLLA linkages was derived as a pseudo first-order reaction:

$$\ln[(DP-1)/DP]=-kt+\ln[(DP_S-1)/DP_S] \qquad (2)$$

where DP and $DP_S$ are the degrees of polymerization of hydrolysis products at time t and being first generated when degradation starts (>0 hour), respectively. Therefore, the distribution of PLLA degradation products in high mass range over 600 m/z of ToF-SIMS can be converted to the corresponding MWD function in two terms ($N_i$ vs. $M_i$) of a statistical averaging MW calculation. Using the MWD function, the results of both $M_n$ and resultant semilog terms, ln[(DP−1)/DP], for kinetics can be calculated. The semilog plots are shown in FIG. 2 as a function of hydrolysis time at two pHs. In these examples, the slope obtained from the linear fitting represents the rate constant of hydrolytic PLLA degradation at the surface of $Ph_3N$/PLLA (20:80 wt %) blend matrices. The results of linear regression of the degradation kinetics represent the characteristic induction phase of the biodegradable poly(α-hydroxy acid) bulk erosion profile.

Data is presented for the hydrolytic degradation of six biodegradable polymers, involving two important classes of biodegradable polymers, in particular polyesters and polyanhydrides, and both homopolymers and random copolymers, using ToF SIMS. Upon hydrolytic degradation of these polymers, low molecular weight oligomers generated during the hydrolytic degradation can be directly detected in ToF SIMS spectra. Further data is presented for the degradation of a model drug delivery system.

The following examples are presented for illustrative purposes and are not to be construed as restricting the claim in any way whatsoever.

EXAMPLE 1

Poly(glycolic acid) (PGA) was obtained from the Davis & Geck Division of American Cyanamid Company; Poly(1-lactic acid) (PLA) (weight average molecular weight 93,000) and poly(dl-lactic-co-glycolic acid) (PLGA) (50:50, molecular weight 50,000–75,000) were purchased from Sigma Chemical Company (St. Louis, Mo.); Poly(fumaric-co-sebacic acid) (PFS) (50:50, average molecular weight 3,046, 20:80, average molecular weight 6,500) and poly (sebacic acid) (PSA, average molecular weight 12,000) were supplied by Brown University; and Physiological solution ISOTON® II was purchased from Coulter Diagnostics in Hialeah, Fla.

PLLA (mol. wt. 100,000) was purchased from Polysciences, Inc. (Warrington, Pa.) and $Ph_3N$ (98%) was purchased from Aldrich (St. Louis, Mo.). A physiological electrolyte buffer solution, ISOTON® II (pH 7.4 at 25° C.), was purchased from Coulter Diagnostics (a division of Coulter Electronics, Inc. Hialeah, Fla.). Sodium carbonate buffer solution (pH 10.0 at 25° C.) was prepared with buffer concentrates (DILUT-IT®) purchased from J. T. Baker Inc. (Phillipsburg, N.J.). HPLC grade chloroform ($CHCl_3$) from Aldrich was used for the preparation of ~2% (w/v) $Ph_3N$/PLLA mixture solutions.

PGA, PLA and PLGA samples were prepared by melt-pressing on aluminum foil. Prior to each melt-press, thick PGA plates were cut to small pieces and washed with an ultrasonic cleaner (from Branson Cleaning Equipment Company, model 5-52) in hexane and chloroform for 10 minutes each. Aluminum foil was pre-cleaned with chloroform. PLA and PLGA were used as received. Samples were pressed at about 200° C. to about 1 mm of thickness. The aluminum foil was peeled off and hydrolysis treatment was conducted immediately.

Polyanhydride samples were prepared by melting polymers on aluminum foil at their melting temperatures. Polymer samples, about 1 mm thick, were pre-cleaned in hexane and vacuum-dried prior to melt. The aluminum foil was peeled off for PSA samples.

$Ph_3N$/PLLA blend matrices from the ~2% (w/v) mixture $CHCl_3$ solutions were spin-coated onto 10×10 mm glass plates at 2000 rpm for 60 seconds using a Headway Research Inc. Model EC 101 spin-coater. The thickness was measured to ca. 390 nm using a profilometer (Alpha-step® 500, Tencor Instruments). The morphology was clear and flat at 700× magnification of scanning electron microscopy (SEM) photomicrographs. In order to confirm the homogeneous distribution of $Ph_3N$ in the matrices, the back-scattering image was measured using a Hitachi S-4000 scanning electron microscope equipped with a back-scattered electron detector. The image of back-scattered electrons was homogeneous, which supports the interpretation that the drug/polymer blend matrices were homogeneous; i.e., no microphase domains of drug were detected in the polymer.

The amount of $Ph_3N$ in $Ph_3N$/PLLA (20:80 wt %) blend matrices was calculated to ca. 0.73 μmole/sample from dissolving the entire film by immersing a sample specimen (film+substrate) in 24 ml of $CHCl_3$ solution at least for 24 hours. The in vitro hydrolysis of $Ph_3N$/PLLA (20:80 wt %) blends was conducted at 37.0±0.2° C. in two pH saline buffer solutions (pH 7.4 and pH 10.0) in order to regulate the local autocatalytic effect of carboxylic acid end groups generated during the treatment. Each blend matrix was immersed in a separate vial pre-filled with 24 ml of buffered solution and reaction vials were placed in an isothermal water bath (Fisher Circulator Model 73) for the predetermined time. All matrices after the allotted times were vacuum-dried at ambient temperature at least for 24 hours before being analyzed. The pH values and the extent of $Ph_3N$ diffusion into the buffers were examined after the hydrolysis treatment using a pH meter (Digital Ionalyzer Model 501 of Orion Research Inc.) and a Milton Roy Spectronic 1201 UV spectrophotometer, respectively. Little change in pH value (±0.1 pH units) was observed and no detectable UV absorption of $Ph_3N$ was measured from the analysis of buffers, from which it can be postulated that the diffusion effect of a drug is minimized in the present model system of drug delivery and the accumulation rate of $Ph_3N$ at the surface of blend matrices represents the amount of a drug available for release of the hydrophobic drug as a function of hydrolysis time.

The hydrolytic degradation of all non-blend matrix polymers was carried out in a physiological buffer solution, ISOTON® II (pH=7.4), at 37.0° C. Each sample was immersed in a separate vial prefilled with 14 ml of ISOTON® II solution and sealed airtight. The reaction vials were immersed in a temperature bath for pre-determined periods depending on the sample's sensitivity to hydrolytic degradation and other properties such as molecular weight and hydrophobicity of the polymer. The hydrolysis time for each polymer was chosen so that the molecular ions of hydrolysis products were observed with good peak intensity. The hydrolysis times of all non-blend polymer samples used in this study are listed in

TABLE 1

| Polymer | Initial Molecular Weight and Time of Hydrolysis Reactions | |
| --- | --- | --- |
| | Molecular Weight | Hydrolysis Time (in hours) |
| PGA | NA | 1 |
| PLA | 93 k | 30 |
| PLGA | 50–75 k | 24 |
| PSA | 12 k | 24 |
| PFS 20:80 | 6.5 k | 3 |
| PFS 50:50 | 3 k | 2 |

Samples after the hydrolysis treatment were vacuum-dried at ambient temperature, and stored in sealed vials filled with argon until ToF SIMS analysis was performed.

ToF SIMS analysis was conducted on a Physical Electronics 7200 time-of-flight secondary ion mass spectrometer equipped with a pulsed cesium ion gun and a channel plate detector. The primary ion gun was operated at 8 keV in all spectral acquisitions. The static mode was used in all acquisitions with the primary ion current of 0.3 pA. The pulse width of primary ion current was 1.0 ns. The total ion dosage in each spectral acquisition did not exceed $1 \times 10^{11}$ ion/cm$^2$. An electron neutralizer was operated during all spectral acquisitions in pulse mode at low electron energy with a target current under 1 μA for charge compensation. A time resolution of 1.25 ns per step was used for good signal-to-noise ratio at high m/z range. The pressure of the main chamber was kept between $10^{-8}$ and $10^{-10}$ torr for each analysis. Data reduction was performed using Physical Electronics TOFPak™ software.

EXAMPLE 2

ToF SIMS Results of Hydrolyzed Polyesters

Ions from polymer chain fragments, with exponentially deceasing intensity, are normally observed in the high mass range ToF SIMS spectra of thick film polymer samples, unless the sample film is prepared as monolayers deposited on metal substrates. Oligomeric ion distributions are not normally observed for thick films due to the entanglement of the long chain molecules in polymer samples. Random chain scission occurs when samples are bombarded by primary ions, which transfers energy to polymer chains near the surface. This process generates fragment ions in ToF SIMS spectra with the characteristic of exponentially decreased intensity with few meaningful peaks due to the decreased possibility of producing high mass fragments.

Upon hydrolysis, polymer chain-lengths are reduced gradually until the oligomers become small enough to desorb from the polymer surface and dissolve in the surrounding liquid phase, where they continue to hydrolyze; yielding monomers as the ultimate reaction products. On the surface of a degraded polymer, the entanglement of the degradation-generated oligomers is greatly reduced because of the decrease in molecular chain-length. During ToF SIMS measurements, low molecular weight oligomers become easier to desorb from the sample surface upon the bombardment of primary ions. Therefore, when degradation occurs at polymer sample surfaces, intact molecular ions of the degradation products can be observed in relatively high mass range of ToF SIMS spectra.

ToF SIMS Results of Hydrolyzed PGA

Figure 3:
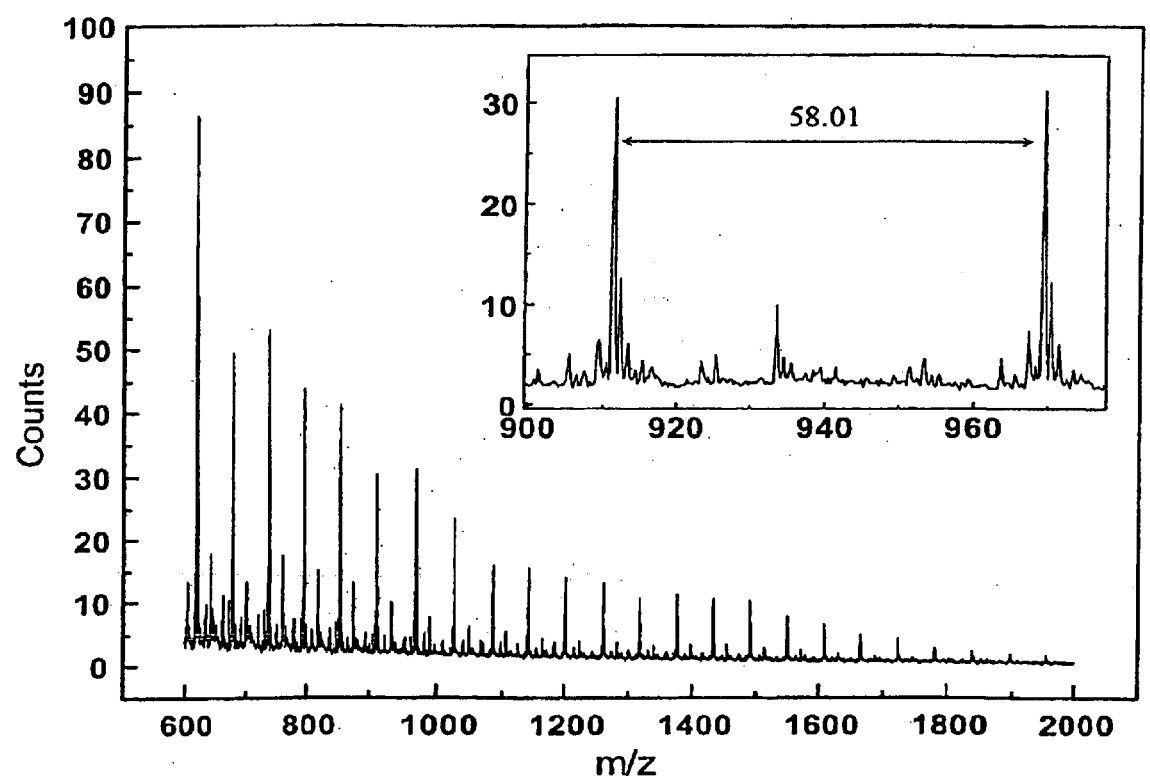
FIG. 3 is a representation of a high mass portion of the ToF SIMS spectra of hydrolyzed PGA.

FIG. 3 shows the high mass portion (600 D to 2000 D) of ToF SIMS spectra of PGA hydrolyzed for one hour. Before the hydrolysis treatment, essentially nothing can be observed in this range except a noisy background. Upon hydrolysis, a peak pattern characterized by the differences due to the mass of the repeat unit of PGA was observed.

All the ions of the major peaks in FIG. 3 have the structure of $[nG+H_2O+Na]^+$, where G stands for the repeat unit of PGA. This indicates that the ions detected from the hydrolyzed PGA sample are in the intact molecules of the hydrolytic degradation product. The sodium ion comes from the external buffer treatment solution and participates in the process of secondary ion formation as an ionization assisting agent. It will be seen that in all samples studied, sodium plays an important role in the ionization process and all species detected in this series contain at least one sodium ion each. It was also observed that, when the concentration of potassium is high enough to promote secondary ion formation of hydrolysis products, a set of molecular ion peaks associated with potassium could be present simultaneously with the series of peaks associated with the sodium ion.

Molecular ions of up to 33 repeat units were observed in ToF SIMS spectra of some samples of hydrolyzed PGA. Small oligomers detected in this study can be traced down to the final hydrolysis product, for example the single glycolic acid molecule associated with one sodium ion.

Figure 4:
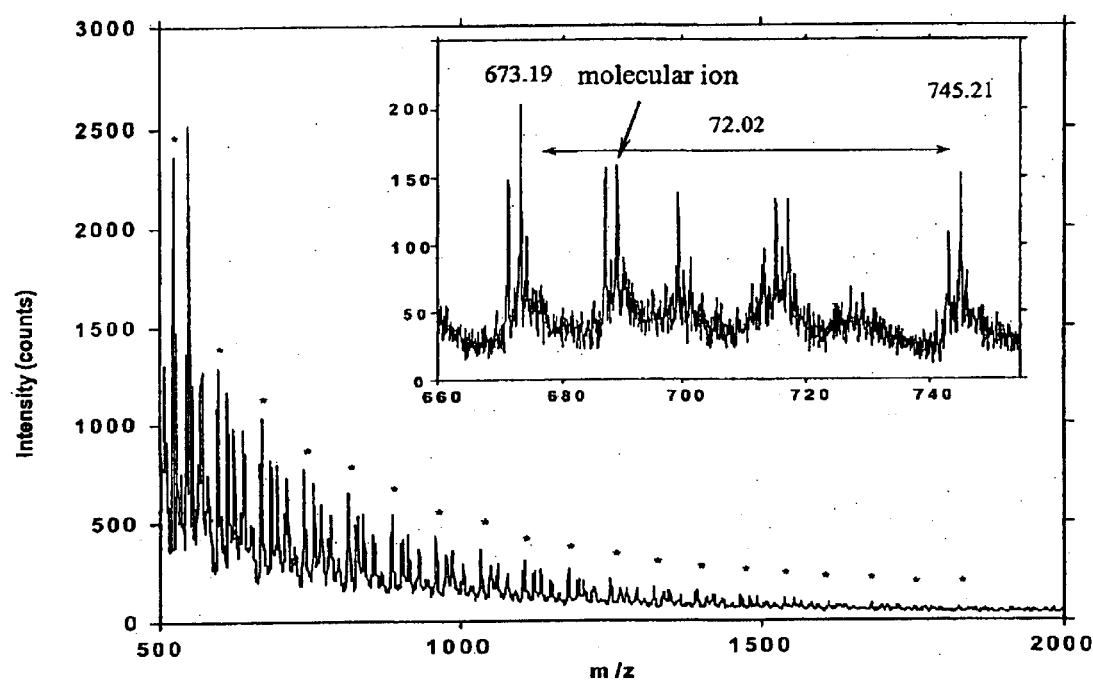
FIG. 4 is a representation of a high mass portion of the ToF SIMS spectra of hydrolyzed PLA.

Table 2 lists the full range of molecular ions that have been detected in this study, with the ions shown in FIGS. 3 and 4 listed in bold.

TABLE 2

Hydrolysis Products of BOA and PLA Observed in ToF SIMS Spectra

| Number of monomers | PGA | m/z | PLA |
|---|---|---|---|
| composition | nG + $H_2O$ | | nL + $H_2O$ |
| 1 | 99 | | 113 |
| 2 | 157 | | 185 |
| 3 | 215 | | 257 |
| 4 | 273 | | 329 |
| 5 | 331 | | 401 |
| 6 | 389 | | 473 |
| 7 | 447 | | 545 |
| 8 | 505 | | 617 |
| 9 | 563 | | 689 |
| 10 | 621 | | 761 |
| 11 | 679 | | 833 |
| 12 | 737 | | 905 |
| 13 | 795 | | 977 |
| 14 | 853 | | 1049 |
| 15 | 911 | | 1121 |
| 16 | 969 | | 1193 |
| 17 | 1027 | | 1265 |
| 18 | 1085 | | 1337 |
| 19 | 1143 | | 1409 |
| 20 | 1201 | | 1481 |
| 21 | 1259 | | 1553 |
| 22 | 1317 | | 1625 |
| 23 | 1375 | | 1697 |
| 24 | 1433 | | 1769 |
| 25 | 1491 | | 1841 |
| composition | nG + $H_2O$ | | nL + $H_2O$ |
| 26 | 1549 | | |
| 27 | 1607 | | |
| 28 | 1665 | | |
| 29 | 1723 | | |
| 30 | 1781 | | |
| 31 | 1839 | | |
| 32 | 1879 | | |
| 33 | 1955 | | |
| 34 | 2013 | | |
| 35 | 2071 | | |
| 36 | 2129 | | |
| 37 | 2187 | | |
| 38 | 2245 | | |
| 39 | 2303 | | |
| 40 | 2361 | | |
| 41 | 2419 | | |
| 42 | 2477 | | |
| 43 | 2535 | | |
| 44 | 2593 | | |
| 45 | 2651 | | |

In addition to the wide distribution of molecular ion peaks, a crest of the molecular ion peaks can also be seen. This crest (1) was first observed in the one hour hydrolysis sample spectra (FIG. 3) at 1400 D to 1500 D, and (2) became more pronounced when it moved to the low mass range gradually as the hydrolysis time increased. This crest represents the most probable molecular weights of hydrolysis products at the particular reaction time. The hydrolytic degradation kinetics can be explored using the data from the ToF SIMS analysis.

ToF SIMS of Hydrolyzed PLA

PLA has the same main chain backbone as PGA plus a methyl group as a side chain. The presence of the methyl group, however, significantly changes the properties of the ester carbon as well as the bulk polymer properties such as morphology and hydrophobicity. These changes are reflected in the characteristic rates of hydrolytic degradation and consequently in the ToF SIMS spectra of hydrolyzed samples. FIG. 3 shows the high mass portion (from 500 D to 2000 D) of ToF SIMS spectra of PLA disc samples hydrolyzed for 30 hours. The star marked peaks are the most intense peak in each repeat pattern. As in the spectra of PGA, each repeat pattern corresponds to one repeat unit of PLA. The intervals between each of the star marked peaks are 72.02 m/z, exactly the mass of one PLA repeat unit.

Molecular ion peaks are observed from the surface of hydrolyzed PLA from the final hydrolysis product (for example, the single lactic acid molecule) up to the oligomer with 25 repeat units of PLA. The intensity of the low mass species (not shown in the figures) becomes lower and lower quickly, this is likely due to the increased diffusibility of the low mass hydrolysis products from the solid sample surface to the hydrolysis solution and the increased solubility as the molecular weight is reduced.

A remarkable difference between PLA and PGA is the hydrolytic degradation rate. The spectra shown in FIG. 4 are PLA hydrolyzed for 30 hours under the same hydrolysis conditions as that for PGA. For PLA samples hydrolyzed in shorter times, good peak patterns of hydrolysis products could not be observed. In addition, there is no peak crest observed at this hydrolysis time, as seen in the ToF SIMS spectra of hydrolyzed PGA (FIG. 3) The intensity of molecular ion peaks is exponentially decreasing as the m/z increases.

TOF SIMS of Hydrolyzed PLGA

Figure 5:
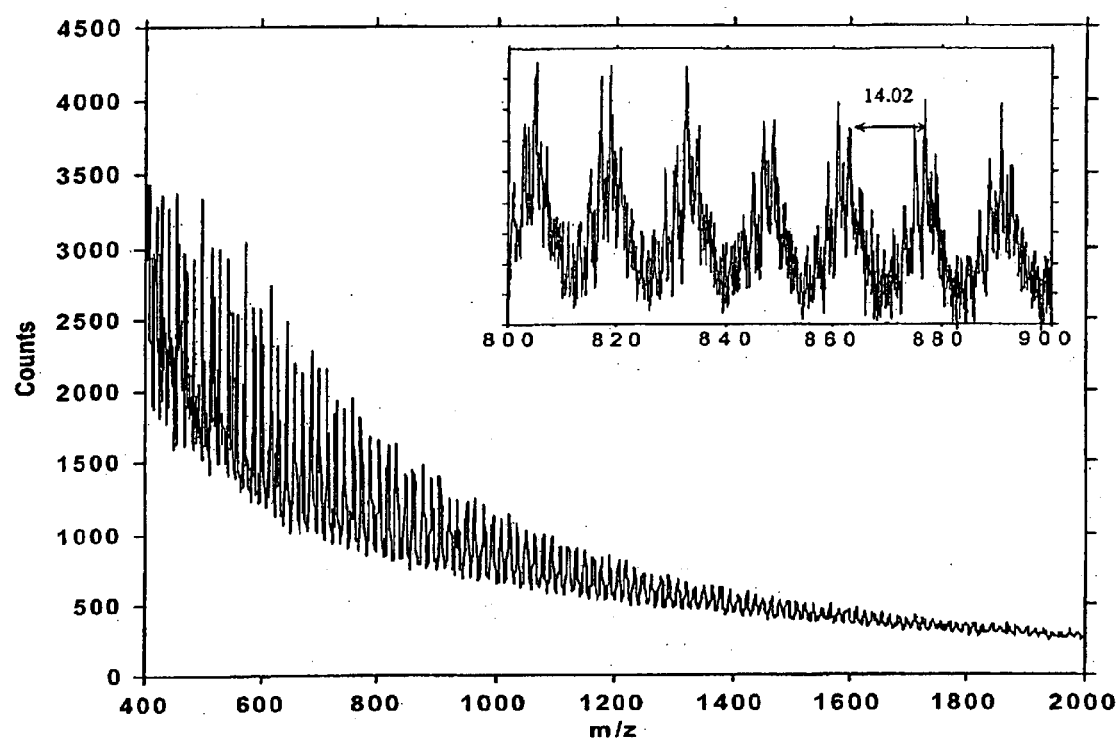
FIG. 5 is a representation of a high mass portion of the ToF SIMS spectra of hydrolyzed PLGA 50:50 copolymer.

FIG. 5 shows the high mass portion (400 D to 2000 D) of the ToF SIMS spectrum of PLGA 50—50 random copolymer hydrolyzed for 24 hours. The pattern of the spectra is obviously more complicated than both the PGA and PLA spectra. Each of the peaks in FIG. 5 consists of a group of peaks (see the inset in FIG. 5). The intervals between the groups are essentially 14 D indicating the repeat pattern is governed by the structural difference between monomeric lactic and glycolic acids. In addition, the most intense peak in each group shifts gradually towards lower m/z so that the overall interval of the repeat pattern is not the exact m/z of one $CH_2$ group over the full range shown in FIG. 5. This complicated pattern can be understood by considering all possible compositions of hydrolysis products of this random copolymer. Table 3 tabulates the m/z values of all possible molecular ion compositions in terms of m/z for low molecular weight oligomers of the hydrolysis products up to 15 PLA repeat units and 12 PGA repeat units.

TABLE 3

Theoretically Predicted PLGA Oligomers of Hydrolysis Products*

| L/G** | 0 | 1 | 2 | 3 | 4 | 5 | 6 | 7 | 8 | 9 | 10 | 11 | 12 |
|---|---|---|---|---|---|---|---|---|---|---|---|---|---|
| 0 | 41 | 99 | 157 | 215 | 273 | 331 | 389 | 447 | 505 | 563 | 621 | 679 | 737 |
| 1 | 113 | 171 | 229 | 287 | 345 | 403 | 461 | 519 | 577 | 635 | 693 | 751 | 809 |
| 2 | 185 | 243 | 301 | 359 | 417 | 475 | 533 | 591 | 649 | 707 | 765 | 823 | 881 |
| 3 | 257 | 315 | 373 | 431 | 489 | 547 | 605 | 663 | 721 | 779 | 837 | 895 | 953 |
| 4 | 329 | 387 | 445 | 503 | 561 | 619 | 677 | 735 | 193 | 851 | 909 | 967 | 1025 |
| 5 | 401 | 459 | 517 | 575 | 633 | 691 | 749 | 807 | 865 | 923 | 981 | 1039 | 1097 |
| 6 | 473 | 531 | 589 | 647 | 705 | 763 | 821 | 879 | 937 | 995 | 1053 | 1111 | 1169 |
| 7 | 545 | 603 | 661 | 719 | 777 | 835 | 893 | 951 | 1009 | 1067 | 1125 | 1183 | 1241 |
| 8 | 617 | 675 | 733 | 791 | 849 | 907 | 965 | 1023 | 1081 | 1139 | 1197 | 1255 | 1313 |
| 9 | 689 | 747 | 805 | 863 | 921 | 979 | 1037 | 1095 | 1153 | 1211 | 1269 | 1327 | 1385 |
| 10 | 761 | 819 | 877 | 935 | 993 | 1051 | 1109 | 1167 | 1225 | 1283 | 1341 | 1399 | 1457 |
| 11 | 833 | 891 | 949 | 1007 | 1065 | 1123 | 1181 | 1239 | 1297 | 1355 | 1413 | 1471 | 1529 |
| 12 | 905 | 963 | 102 | 1079 | 1137 | 1195 | 1253 | 1311 | 1369 | 1427 | 1485 | 1543 | 1601 |
| 13 | 997 | 103 | 109 | 1151 | 1209 | 1267 | 1325 | 1383 | 1441 | 1499 | 1577 | 1615 | 1673 |
| 14 | 1049 | 110 | 116 | 1223 | 1281 | 1339 | 1397 | 1455 | 1513 | 1571 | 1629 | 1687 | 1745 |
| 15 | 1121 | 117 | 123 | 1295 | 1353 | 1411 | 1469 | 1527 | 1585 | 1643 | 1701 | 1759 | 1817 |

Figure 6:
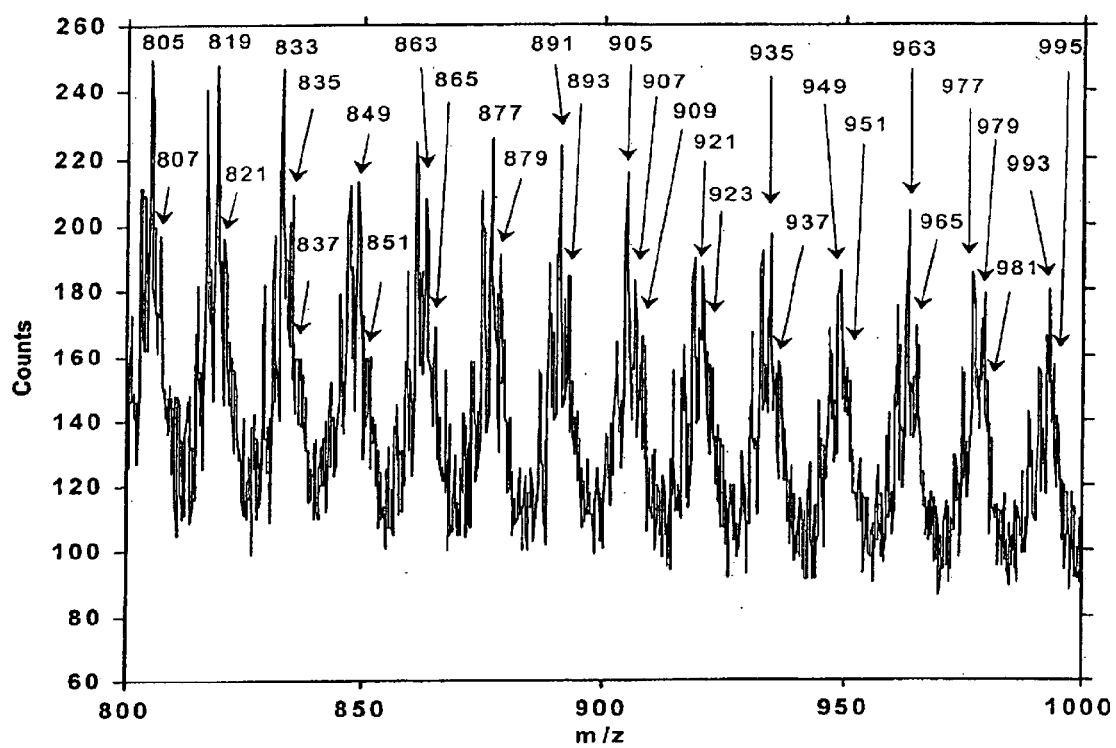
FIG. 6 is a representation of the ToF SIMS spectra of hydrolyzed PLGA from 800 D to 1000 D. Number marked peaks are molecular ion peaks.

*The hydrolysis products are tabulated in m/z with the ion composition of $[xL + yG + H_2O + Na]+$, where L and G represent the monomeric repeat unit of lactic acid or glycolic acid, respectively. Ions in bordered cells are shown in FIG. 6. Ions in bold become too low in intensity.
**The number of lactic acid monomers in each oligomer molecule is shown in rows and the number of glycolic acid monomers is shown in columns.

These ions represent the structure of intact molecules which would then be cationized with at least one sodium ion each. All molecular ions listed in Table 3 are observed in the ToF SIMS spectra except those with high composition ratios of PGA over PLA repeat units. This is because PGA is more sensitive to hydrolysis than PLA. To illustrate this fact, ions in the framed cells (oligomer molecular ions from 800 D to 1000 D) are shown and marked with m/z values in FIG. 6. It shows that most peaks shown in the spectra are molecular ion peaks with the most intense peak shifts to the left in each cluster due to the composition of the molecular ions. In fact, the most intense peak in each cluster is always corresponding to the ion with the smallest number of glycolic acid repeat units and the largest number of lactic acid repeat units. The peak intensities for the ions in the shaded cells of Table 3 consisting of larger ratio of glycolic acid repeat units than the ions to their left, become too low to be detected.

The relative intensity of molecular ion peaks also serves as an indication of the relative hydrolysis rate of the two components of the copolymer. PGA hydrolyzes faster than PLA as observed in the homopolymers of PGA and PLA; therefore, fewer PGA repeat units remain in the hydrolysis products. No oligomers with only PGA repeat units were observed while oligomers with pure PLA were observed as the most intense peak in its group (peaks of 833, 905 and 977 D in FIG. 6, for example).

Figure 7:
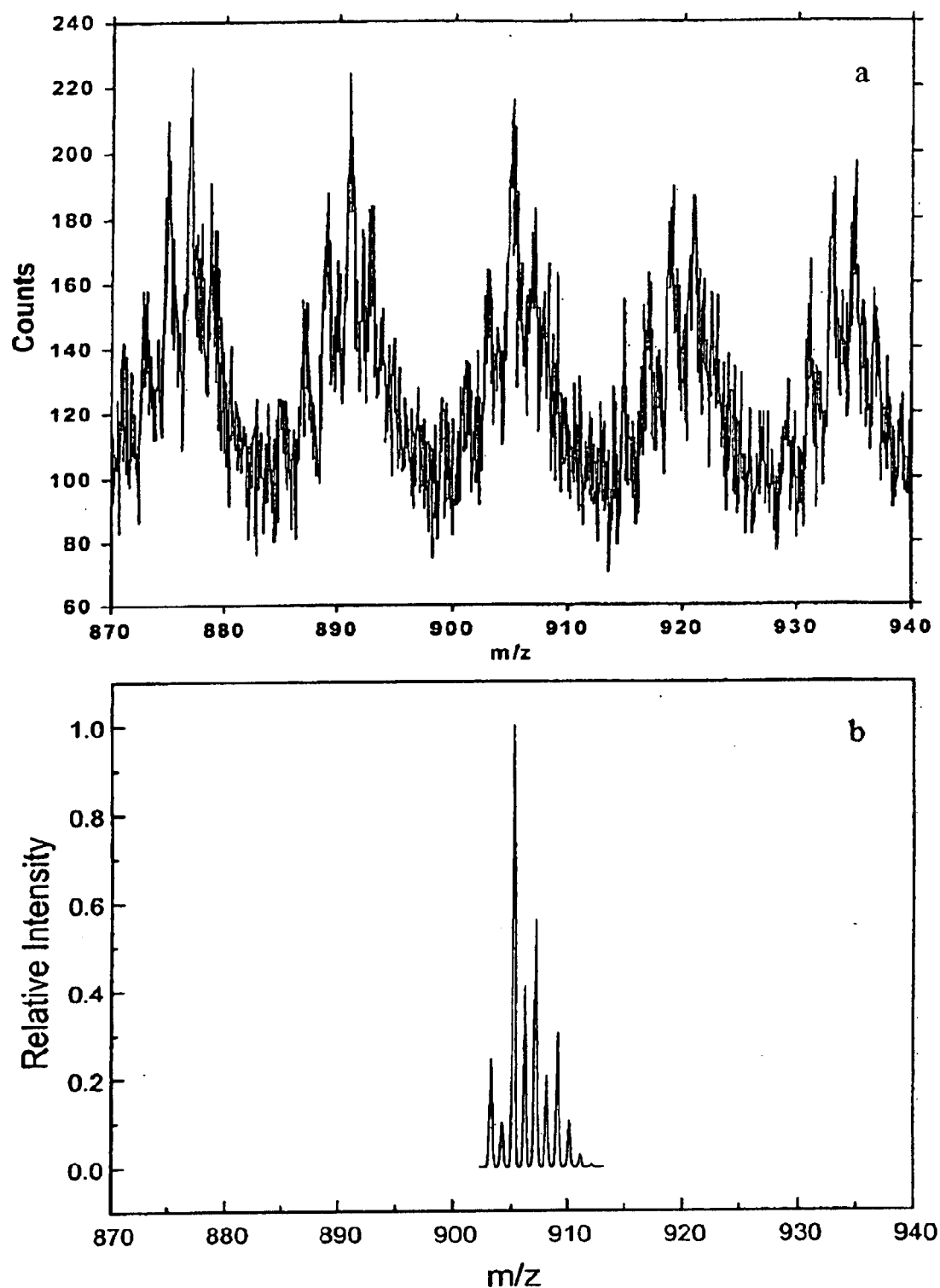
FIG. 7 is a comparison of a group of molecular peaks in the ToF SIMS spectra with the theoretically calculated mass spectra.

FIG. 7 exemplifies the composition of the molecular ion peaks by comparing one of the peak groups with the theoretically calculated spectra. FIG. 7a is a small portion of the spectrum shown in FIG. 6 and FIG. 7b is the corresponding molecular ion peak region theoretically calculated using Googly (Copyright 1994, Andrew Proctor), taking the elemental isotopic abundance into account. The match in peak position and relative intensity between the experimentally recorded spectra and the theoretically predicted one supports the assignment of the peaks. FIG. 6 indicates that all major peaks in the ToF SIMS spectra of hydrolyzed PLGA copolymer are intact molecular ions of the hydrolysis products.

PGA is the simplest biodegradable poly($\alpha$-hydroxy acid) with high crystallinity and hydrophilicity. PLA is only one methyl group different from the structure of PGA as the side-chain on the $\alpha$-carbon, which causes a remarkable change in its properties from PGA, in addition to the formation of two monomeric enantiomeric structures, and copolymers of different tacticities. For example, the crystallinity of both P(d)LA and P(l)LA is lower than PGA and the presence of the methyl group in PLA significantly decreases its reactivity toward ester hydrolysis mechanism due to the electron donating effect, resulting in the global decrease in hydrophilicity. As a result, the increased hydrophobicity can reasonably explain the relatively slower hydrolytic degradation of PLA and makes PLA dissolve well in common organic solvents in contrast to PGA, which is soluble only in hexafluoroisopropanol. Hence, these properties can influence not only each own hydrolytic degradation properties, but also the fragmentation process upon the bombardment of the primary ions.

Therefore, the difference in each hydrolytic degradation rates between PLA and PGA can be supported by the observation from ToF SIMS spectra of hydrolyzed PLGA 50:50 copolymer. As shown in FIG. 6, peaks consisting of more PLA repeat units and less PGA repeat units are always even more intense than those consisting of more PGA repeat units; indicating that PLA segments are less reactive to hydrolysis than PGA segments. The overall trend of molecular ion peak intensities of the hydrolyzed PLGA copolymer is similar to that of hydrolyzed PLA spectra (FIG. 4).

EXAMPLE 3

ToF SIMS of Hydrolyzed Polyanhydrides

Figure 8:
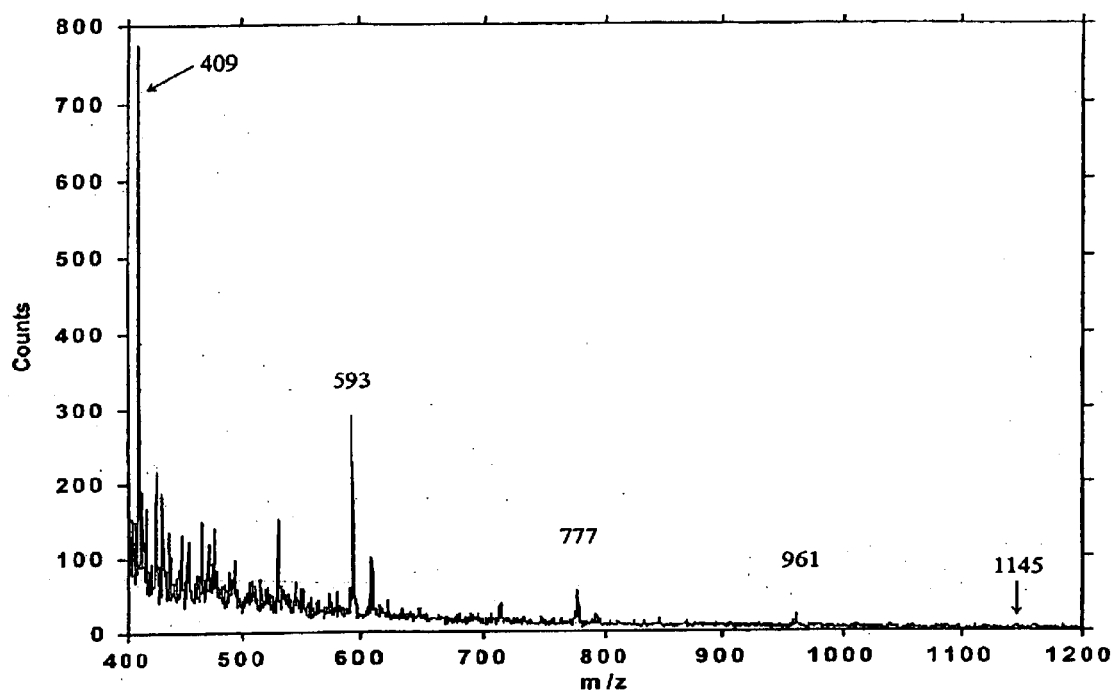
FIG. 8 is a representation of a high mass portion of the ToF SIMS spectra of hydrolyzed PSA.

Polyanhydrides are significantly different from polyesters in that the anhydride linkage in the backbone is more vulnerable to attack by water than the ester bond. This leads to faster hydrolysis rates for polyanhydrides and causes a narrow molecular weight distribution of the hydrolysis products. FIG. 8 shows the ToF SIMS spectra of hydrolyzed PSA from 400 D to 1200 D. Molecular ion peaks are the most dominant one in each repeat pattern, indicating that the anhydride bond is far easier to break than the alkyl chain. Intact molecular ions observed are from the single sebacic acid molecule up to the oligomer of six PSA repeat units. The single sebacic acid molecule, which is the first member in the series of hydrolysis products, however, is small enough to be dissolved in the hydrolysis solution. Hence, very few of them stay on the surface of samples after the hydrolysis experiments. Therefore, the first significant molecular ion peak is the one that consists of two PSA repeat units. All observed oligomers of the hydrolysis products are listed in Table 4 in the form of actually observed ions, consisting of the intact molecules attached with a sodium ion.

TABLE 4

Molecular Ion Beaks Observed in Hydrolysis Products of Polyanhydrides

| # of repeat | m/z | | |
|---|---|---|---|
| 1 | 225 | 225 | 225 |
| 2 | 409 | 409 | 409 |
| 3 | 593 | 593 | 593 |
| 4 | 777 | 777 | 777 |
| 5 | 961 | 961 | |
| 6 | 1145 | | |

* Molecular ion peaks of the final products are very low intensity, not shown in the figures.

Remarkably different from the polyesters, the intensity of molecular ion peaks drops quickly and exponentially. It can be seen from the spectra in FIG. 7 that there would be no species larger than the six-repeat-unit oligomer detectable on the sample surface.

ToF SIMS of Hydrolyzed PFS Copolymers

Figure 9:
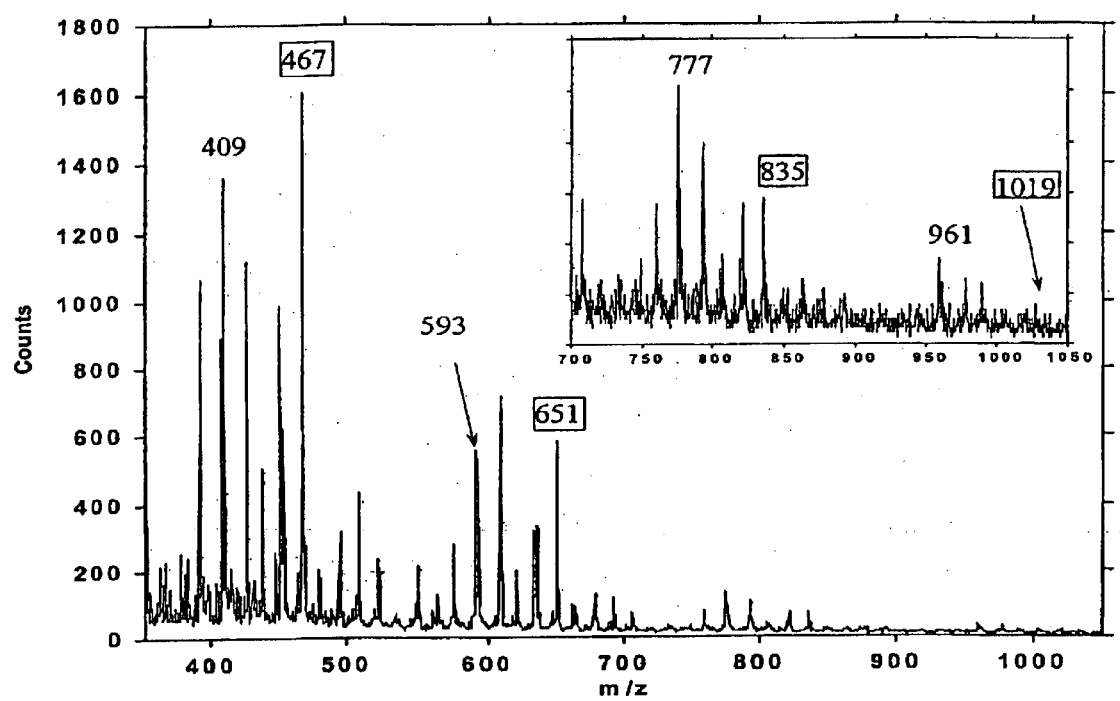
FIG. 9 is a representation of a high mass portion of the ToF SIMS spectra of PFS 20:80 copolymer before hydrolysis treatment.

Two random copolymers of PFS have been studied, in particular 50:50 and 20:80 by weight percentage of fumaric acid to sebacic acid ratio. The initial molecular weight of 50:50 PFS sample is about 3000 by number average molecular weight, and that of 20:80 PFS sample is about 6000. Considering the molecular weights of the repeat units being 98 and 184 for furmaric acid and sebacic acid, respectively, the degree of polymerization is quite low for both copolymers, approximately 20 for the 50:50 copolymer and 36 for the 20:80 copolymer. It was expected that unreacted oligomers might be detected in the medium mass range of ToF SIMS spectra of unhydrolyzed samples. FIG. 9 shows the ToF SIMS spectra of 20:80 copolymer before hydrolysis from 350 D to 1050 D. As it is expected, significant ion series were detected up to 1000 D. The ion sequence of 467 D, 651 D, 835 D and 1019 D (framed-number marked in FIG. 9) has the composition of $[F+nS+H]^+$, in which F and S represent the repeat unit of fumaric acid and sebacic acid, respectively. However, in addition to the fragment ion peaks, the molecular ion peak series of 409 D, 593 D, 777 D and 961 D are also present. The composition of this series conforms to the ion structure $[nS+H_2O+Na]^+$, indicating that the copolymer has already partially hydrolyzed during storage. Note that the relative intensity of the two series changes as the m/z increases. The fact that the relative intensity of the molecular ion peak series to the fragment series increases as the m/z increase indicates that the distribution of molecular oligomer ions is independent from the fragment ion distribution.

Figure 10:
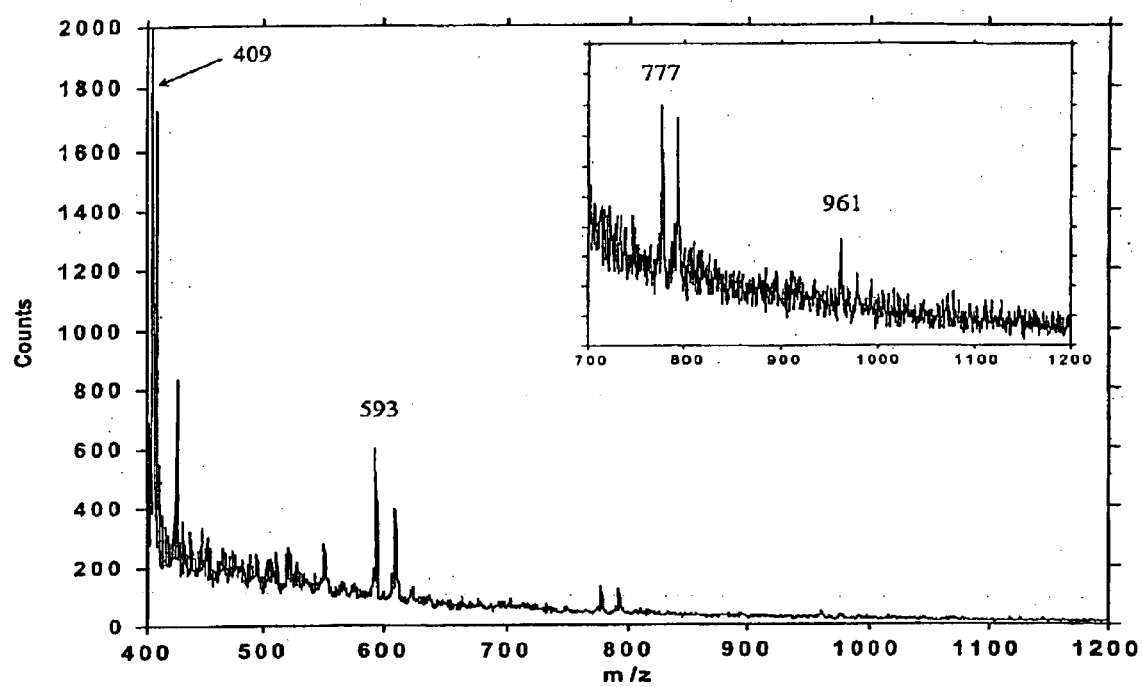
FIG. 10 is a representation of a high mass portion of the ToF SIMS spectra of hydrolyzed PFS 20:80 copolymer.

Upon hydrolysis treatment, the fumaric acid repeat unit could not be detected from any hydrolysis products. FIG. 10 shows the ToF SIMS spectra of 20:80 copolymer from 400 D to 1200 D. The spectra of hydrolyzed PFS copolymer are almost the same as that of hydrolyzed PSA, indicating that fumaric acid component in the random copolymer chain sequence is far more sensitive to a hydrolysis environment, and hydrolyzes faster than the PSA sequences. The marked peaks in FIG. 10 have exactly the same ion composition as the hydrolysis products of PSA. The difference between the spectrum and that of the product of hydrolyzed PSA is that the largest molecule detected in 20:80 PFS copolymer has five sebacic acid repeat units while the largest molecule detected in PSA has six sebacic acid repeat units, in spite of the shorter hydrolysis time for the copolymer samples. This is an additional indication of the faster hydrolysis property of the PFS copolymer compared to the homopolymer of PSA.

Figure 11:
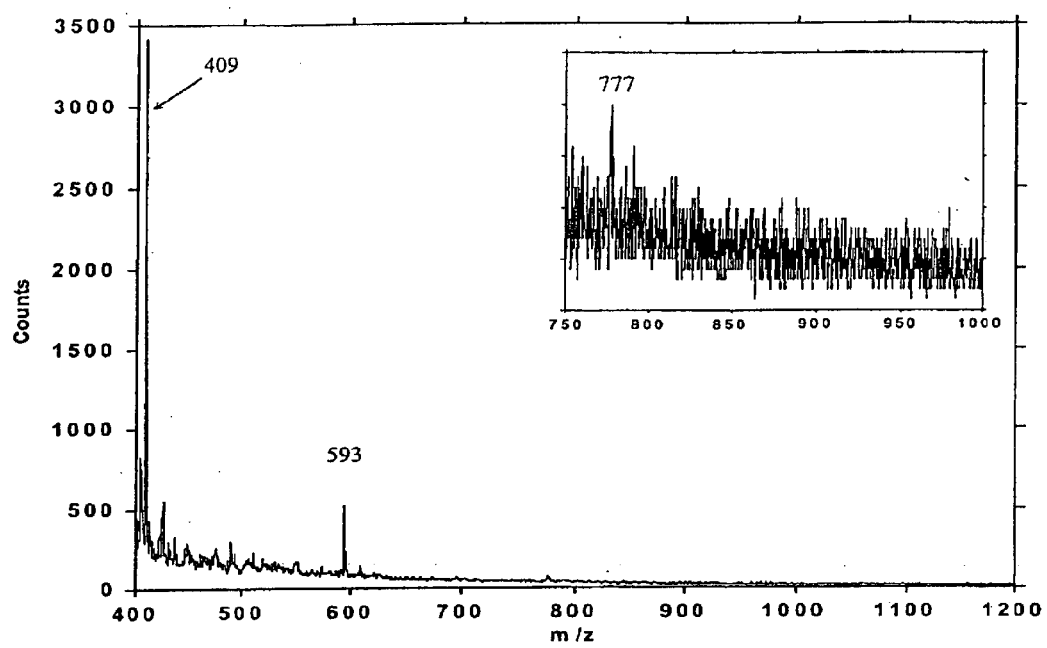
FIG. 11 is a representation of a high mass portion of the ToF SIMS spectra of hydrolyzed PES 50:50 copolymer.

Similar results were observed for the 50:50 PFS copolymer. FIG. 11 shows the ToF SIMS spectra of the hydrolyzed sample from 400 D to 1200 D. Similar to the 20:80 sample, only low molecular weight oligomers of PSA were observed and products are more narrowly distributed to lower molecular weights. The largest oligomer molecule observed in the two hour hydrolyzed sample of this copolymer has only four sebacic acid repeat units. In addition, the intensity of the molecular ion peaks decreases much faster than the 20:80 copolymer and the homopolymer of PSA, indicating higher hydrolysis rate is associated with higher fumaric acid content.

Figure 12:
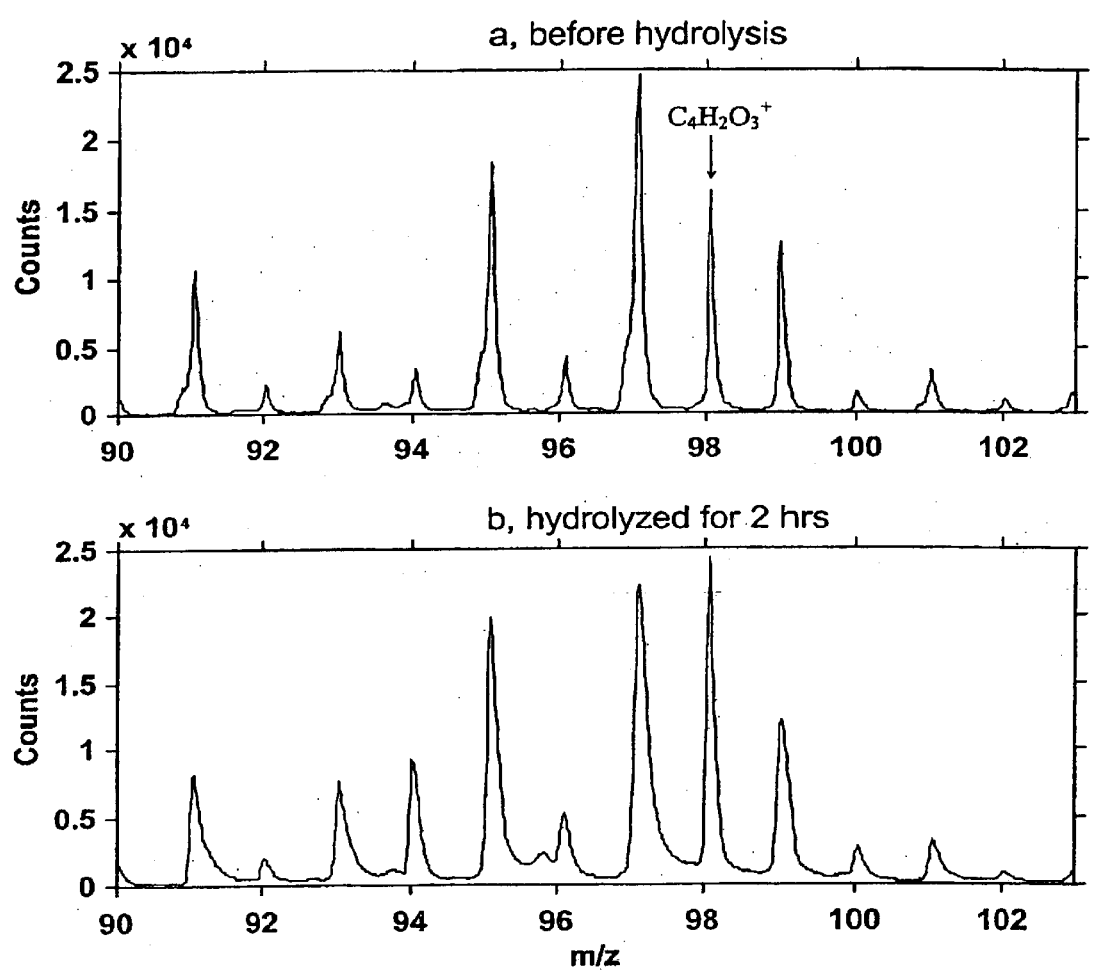
FIG. 12 is a comparison of the low mass portion (90 D to 103D) of the ToF SIMS spectra of PFS copolymer before and after hydrolysis.

Although there was no fumaric component detected in the hydrolyzed sample of both the two PFS copolymers, fragment ions from fumaric acid repeat units were indeed detected in all cases, indicating that the fumaric acid repeat unit is released from the polymer chain sequence as a whole unit during the hydrolytic degradation. FIG. 12 shows the fragment peaks of fumaric acid single unit before and after hydrolysis for two hours, Peaks of 97 D, 98 D and 99 D are the ions of $[F-H]^+$, $F^+$ and $[F+H]^+$, respectively. The increased relative intensities of $F^+$ to other peaks may also indicate the contribution of hydrolytic cleavage of fumaric acid bonds.

Both PSA and PFA (poly(fumaric acid)) are highly crystalline materials. It has been determined that the crystallinity of homopolymers of PSA and PFA are 66%, respectively. The crystallinity of their copolymers decreases depending on the composition of the copolymer, but it is no lower than 38% for all compositions. The samples of the polyanhydrides studied in this work, therefore, cannot be made by solution-casting. One of the concerns for the melt-cast sample preparation procedure is the possibility of oxidation or cross-linking of the double bond in fumaric acid at elevated temperatures. There is no evidence found, however, that the double bond in fumaric acid has been severely changed. The intense fragments of fumaric acid at 97 D, 98 D and 99 D, corresponding to $[F-H]^+$, $F^+$ and $[F+H]^+$, are evidence of the existence of an abundance of unreacted fumaric acid structures (FIG. 12a). This structure was also detected in high intensity after the hydrolysis treatments (FIG. 12b), suggesting the basic repeat units of fumaric acid was not changed during the hydrolysis reaction either.

However, fragment ions containing multiple fumaric acid repeat units were never detected in this study. In the ToF SIMS spectra of PFS samples without hydrolysis treatments, only one fumaric acid repeat unit was detected in fragment sequences containing fumaric acid, whereas fragments with up to five sebacic acid repeat units were detected. The molecular ion peak series of hydrolysis products were found in both spectra of 20:80 and 50:50 copolymer samples before hydrolysis treatments. These molecular ion peak sequences consist of only sebacic acid monomers, suggesting that the anhydride bond of fumaric acid is more sensitive to hydrolysis than the anhydride bond of sebacic acid. There are two factors each may play an important role in this issue. One is the hydrophilicity. Sebacic acid contains a highly hydrophobic aliphatic structure while the structure of fumaric acid is highly hydrophilic. This may result in the hydrolytic degradation during storage to occur selectively at the fumaric acid sequence. The other factor is the conjugative property of the fumaric acid structure. With two carboxylic acid groups bridged by a double bond, fumaric acid forms a conjugated structure. This conjugated system increases the reactvity of the carboxylic acid carbon towards nucleophilic reactions.

The differences in hydrolytic degradation rates among the three polyanhydrides can be seen by the hydrolysis time and the hydrolysis products illustrated in the ToF SIMS spectra. Table 4 lists all molecular ions detected in the hydrolyzed samples of all three polyanhydrides. The largest molecule of PSA hydrolysis products has six sebacic acid repeat units while the 20:80 copolymer has five and the 50:50 copolymer has four, although shorter hydrolysis time were used for the PFS copolymers. Furthermore, the intensities of the most intense molecular ion peaks are about 3500, 2000 and 800 for 50:50, 20:80 and the homopolymer of PSA, respectively. Therefore, the molecular ion peaks decrease faster for copolymers that have higher fumaric acid content.

EXAMPLE 4

Information for Kinetics Analysis

As mentioned above in Example 2, a crest of the molecular ion peaks exists which grows and moves toward the low mass end when the hydrolysis time increases. Under the assumption that this crest represents the most probable molecular weight distribution of the hydrolysis products, the average molecular weight of the hydrolysis products can be calculated from the ToF SIMS spectra. The average molecular weight obtained from ToF SIMS is a function of hydrolysis time. A linear relationship between the apparent molecular weight and the hydrolysis time has been observed. This observation indicates that the ToF SIMS spectra of hydrolyzed samples carry information about the hydrolytic degradation process of the polymer, which can be used in kinetics and mechanism analysis of hydrolytic degradation of the polymer. Based on this, ToF SIMS studies of the degradation kinetics can be carried out.

Figure 13:
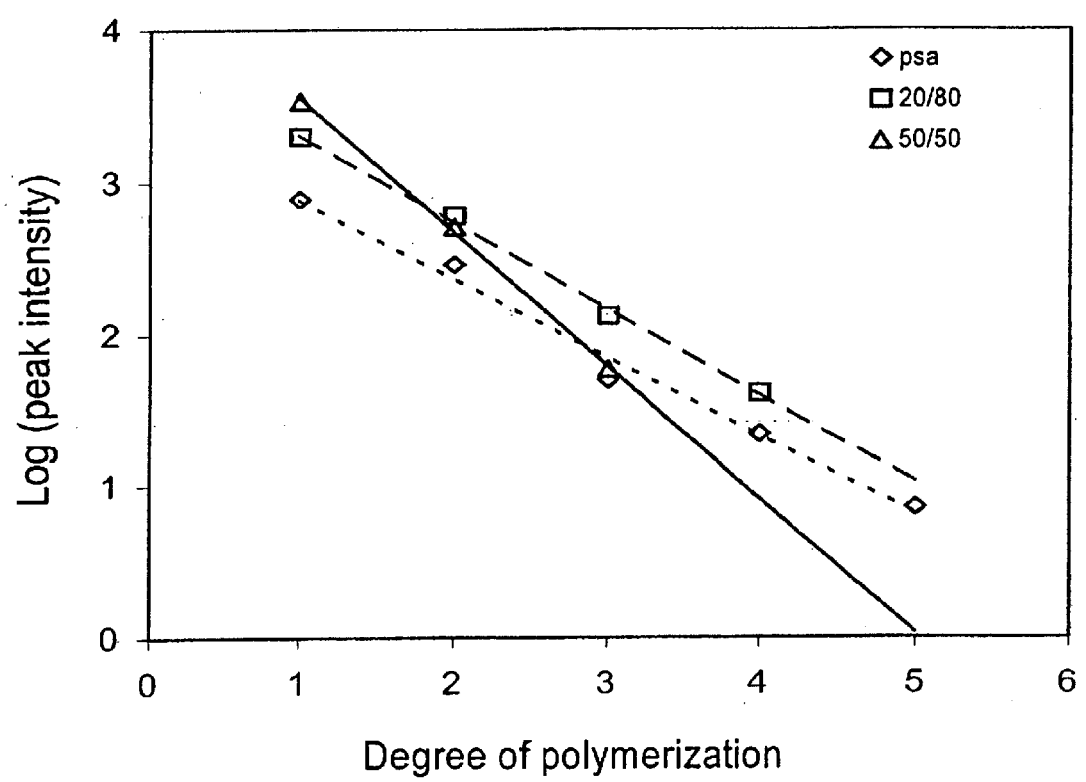
FIG. 13 is a plot of log molecular ion peak intensity of hydrolyzed polyanhydrides versus degree of polymerization of the hydrolysis products.

The size of the largest molecule of the hydrolysis products of polyanhydrides decreases as the content of fumaric acid in the copolymer increases, and the molecular ion peak intensity decreases faster accordingly. This is directly related to the hydrolytic degradation property of the polymer. Also, the intensity of the molecular ion peaks decreases exponentially. When the logarithm of the intensity of the molecular ion peak is plotted versus the degree of polymerization, a good linear relationship exists, as shown in FIG. 13. The slope of the plot reflects how fast the molecular ion peak intensity decreases, and where the line crosses with the line of Log(y)=0, which indicates the molecule of the size marked by the cross point could not practically exist anymore. The slopes of the straight lines have a proportional correlation with the hydrolytic degradation rates. Therefore, the hydrolytic degradation rate can be quantitatively described by this parameter.

EXAMPLE 5

To determine the concentration of $Ph_3N$ at the surface, peak intensities representative of the drug and polymer components from the spectrum of untreated $Ph_3N$/PLLA blend matrices were integrated over two mass ranges: 53~59 D for $[C_3H_4O]^{.+}$=56 D of PLLA and 241~267 D for $[MH]^+$=246 D of $Ph_3N$ (M=$Ph_3N$ in this example). In this study, the fragment ion peak, $[C_3H_4O]^{.+}$=56.0264 D, from the PLLA repeat unit was used as an internal standard to quantify the surface concentration of $Ph_3N$. The ratio of $[MH]^+$ peak intensity divided by the peak intensity of $[C_3H_4O]^{.+}$ was related to the total amount of $Ph_3N$ incorporated in the matrices, and was considered as proportional to the surface concentration of $Ph_3N$. A standard calibration curve was developed (not shown). Good linearity ($R^2$=0.9984, A=8.92E-4 in Y-0.00768=AX) was obtained from a concentration ratio (X) of 10:90 drug to polymer wt % up to 40:60.

Figure 14:
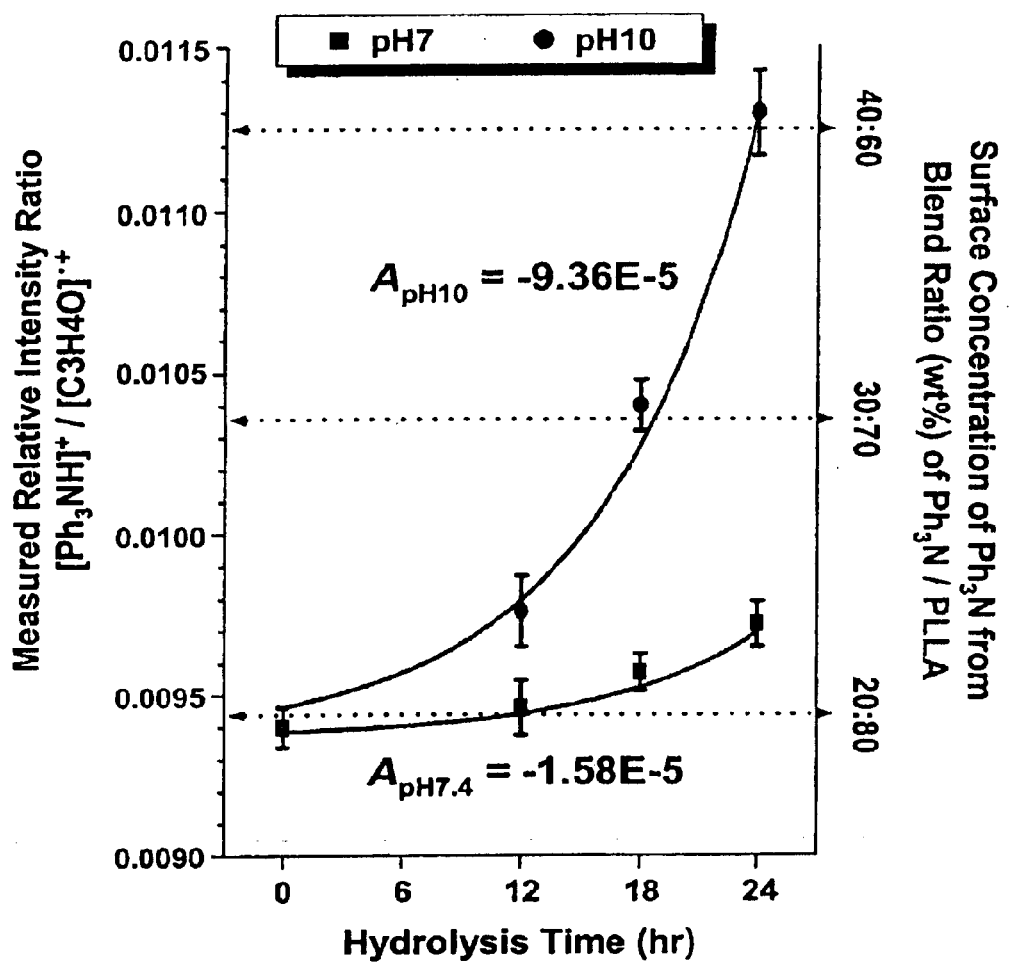
FIG. 14 is a graphical representation of the concentration of $Ph_3N$ accumulated at the surface of $Ph_3N/PLLA$ (20:80 wt %) blend matrices as a function of hydrolysis time in two pH buffered conditions, respectively.

A peak at 246 m/z in the spectrum of pure PLLA was observed to overlap with $[MH]^+$=246 D. The relative intensities, [a peak at 246 m/z]/$[C_3H_4O]^{.+}$, of pure PLLA matrices were measured after the hydrolysis under two different pH buffered conditions for 24 hours, respectively: 2.62E-3 for pH 7.4 and 2.59E-3 for pH 10.0. They indicate that the relative intensity of the peak at 246 m/z ratioed to the intensity of $[C_3H_4O]^{.+}$ in pure PLLA is independent of pH and hydrolysis time. Therefore, the change in the ratio of intensities, 246 m/z divided by 56 m/z, was used as a measure of release profiles that represent a change in surface concentration of $Ph_3N$. The surface concentration of $Ph_3N$ from the 20:80 wt % blend matrices has been measured as a function of hydrolysis time at two buffered pHs and compared to the corresponding measured relative intensity ratio from a series of $Ph_3N$/PLLA blend matrices in FIG. 14 for evaluating the cumulative amount of $Ph_3N$. The curves were fit with an empirical exponential expression, $([Ph_3NH]^+/[C_3H_4O]^{.+})$=9.37E-3+Ae^(t/7.94): $A_{pH10}$=-9.36E-5 for pH 10.0 and $A_{pH7.4}$=-1.58E-5 for pH 7.4. (Right Y axis) Surface concentration of $Ph_3N$ was obtained from the standard calibration curve for surface concentration of $Ph_3N$. The extent of change in accumulation rate of $Ph_3N$ ($A_{pH10}$=5.92×$A_{pH7.4}$) is more than two times greater than the corresponding change in hydrolytic degradation rate of PLLA ($k_{pH10}$=2.67×$k_{pH7.4}$) at the surface of $Ph_3N$/PLLA (20:80 wt %) blend matrices.

These data demonstrate that the oligomers desorb from the sample surface upon the bombardment and ionization, in the form of intact molecules, usually attached with an alkali metal ion. In most cases, the molecular ion peak is the most intense peak in each repeat pattern of ToF SIMS spectra of hydrolyzed polymers.

From the foregoing, it will be obvious to those skilled in the art the various modifications in the above-described methods, and compositions can be made without departing from the spirit and scope of the invention. Accordingly, the invention may be embodied in other specific forms without departing from the spirit or essential characteristics thereof.

Present examples and embodiments, therefore, are to be considered in all respects as illustrative and not restrictive, and all changes which come within the meaning and range of equivalency of the specifications are therefore intended to be embraced therein.

We claim:

1. A method for determination of reaction kinetics of surface degradation of a biodegradable polymer comprising the steps of:

provimg the biodegradable polymer;

initiating degradation of the polymer to produce degradation products;

at a plurality of time points following initiation of the degradation, subjecting the polymer in which degradation has been initiated to ToF SIMS spectral analysis;

obtaining a molecular weight distribution of the degradation products as a function of time from ToF SIMS spectra;

from the molecular weight distribution, calculating the degree of polymerization of the degradation products as a function of time; and calculating the rate of surface degradation of the polymer from the degree of polymerization of the degradation products over time.

2. The method of claim 1 wherein the polymer is selected from the group consisting of polyesters, polyanhydrides, copolymers of polyesters and polyanhydrides and mixtures thereof.

3. The method of claim 2 wherein the polyester is selected from the group consisting of poly($\alpha$-hydroxy acids), poly($\beta$-hydroxy acids), poly($\alpha$-malic acids), pseudo poly($\alpha$-amino acids), copolymers thereof and mixtures thereof.

4. The method of claim 2 wherein the polyanhydride is selected from the group consisting of homo-polyanhydrides of sebacic acid, homo-polyanhydrides of fumaric acid, random co-polyanhydrides of sebacic and fumaric acids, and mixtures thereof.

5. The method of claim 1 wherein the step of initiating degradation comprises solvating the polymer.

6. The method of claim 1 wherein the step of initiating degradation comprises dissociating the polymer.

7. The method of claim 1 wherein the step of initiating degradation comprises hydrolyzing the polymer.

8. The method of claim 7 wherein the step of hydrolyzing comprises contacting the polymer with at least one saline buffer having a pH between about 2.0 and about 12.0, wherein the saline buffer contains an ion selected from the group consisting of phosphate, acetate, carbonate, biphthalate and mixtures thereof.

9. The method of claim 1 wherein the step of initiating degradation comprises dissolving the polymer.

10. The method of claim 1 wherein the step of initiating degradation comprises oxidizing the polymer.

11. The method of claim 1 wherein the step of initiating degradation comprises reducing the polymer.

12. The method of claim 1 wherein the step of initiating degradation comprises photolysing the polymer.

13. The method of claim 1 wherein the step of initiating degradation comprises spinodally decomposing the polymer.

* * * * *